United States Patent [19]
Klementi et al.

[11] 3,992,175
[45] Nov. 16, 1976

[54] METHOD OF AND DEVICE FOR CHROMATOGRAPHIC SEPARATION OF FLUID MIXTURES INTO FRACTIONS

[76] Inventors: Toe Jokhannesovich Klementi, ulitsa Pukhkekodu tee, 46, kv. 1; Toivo Elmar-Jokhannesovich Kruusimagi, ulitsa Tiiva, 18, kv. 1; Jüri Arturovich Veisserik, ulitsa Mustamyae tee, 193, kv. 84, all of Tallin, U.S.S.R.

[22] Filed: Dec. 1, 1975

[21] Appl. No.: 636,651

Related U.S. Application Data

[63] Continuation of Ser. No. 559,558, March 18, 1975, abandoned.

[30] Foreign Application Priority Data
Feb. 11, 1974 U.S.S.R. .............................. 1995195
Mar. 15, 1974 U.S.S.R. .............................. 2005441

[52] U.S. Cl. ....................................... 55/67; 55/197
[51] Int. Cl.² ............................................ B01D 15/08
[58] Field of Search .................... 55/67, 197, 386; 210/31 C, 198 C

[56] References Cited
UNITED STATES PATENTS 3,220,164  11/1965  Golay ....................................... 55/67
3,455,090  7/1969  Deford .................................. 55/67
3,514,262  5/1970  Ayers .............................. 55/386 X
3,698,156  10/1972  Dirian ..................................... 55/67
3,926,589  12/1975  Klementi ................................ 55/67

*Primary Examiner*—John Adee
*Attorney, Agent, or Firm*—Holman & Stern

[57] ABSTRACT

A method of and a device for chromatographic separation of fluid mixtures into fractions by means of circulation of a continuously fed mixture in a system of several separating columns adapted for simultaneous passing of two independent fluid streams through separate series-connected parts of column system with a synchronized replacement of the inlet and outlet points of the fluid streams and inlet point of the mixture along the columns, comprising in accordance with the present invention, preliminary separation of the mixture by means of circulation in a system of at least three columns into two fractions being discharged from said system by two separate fluid streams; with subsequent passing of one or both streams containing the preliminarily separated fraction in the form of a mixture of substances through one or two additional separating columns respectively, wherein the fraction is separated into narrower fractions or individual components.

5 Claims, 13 Drawing Figures

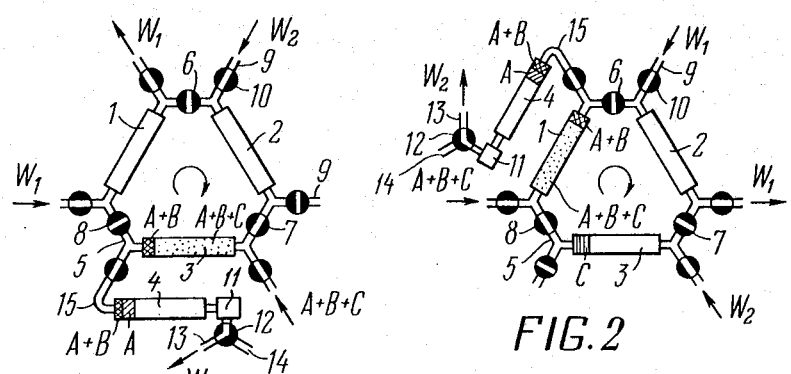
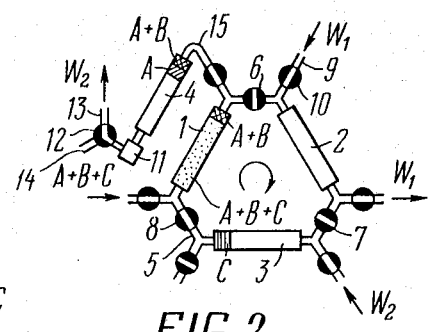
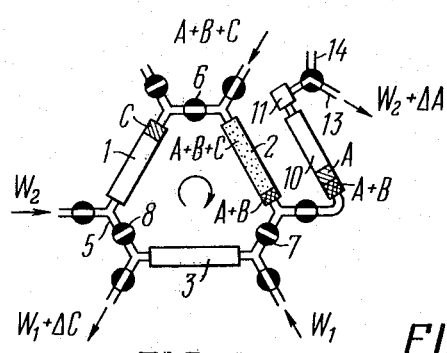
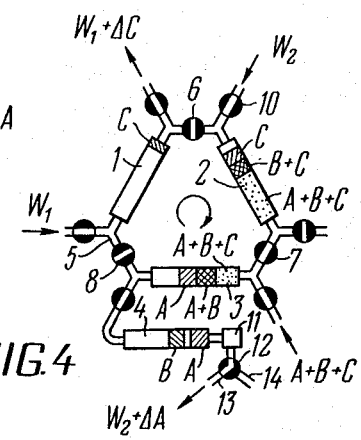
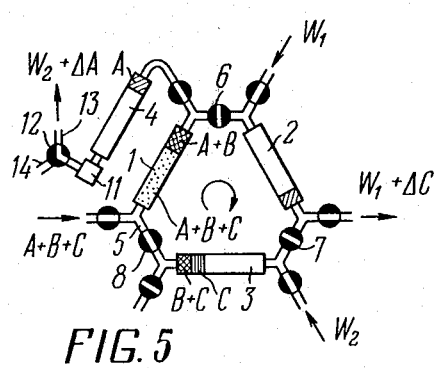
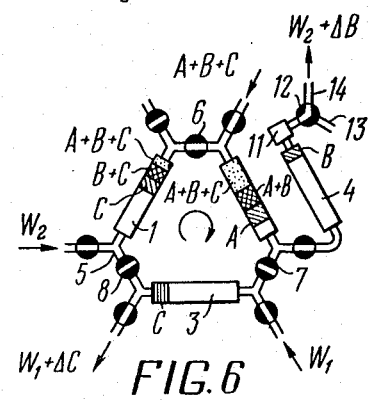

METHOD OF AND DEVICE FOR CHROMATOGRAPHIC SEPARATION OF FLUID MIXTURES INTO FRACTIONS

This is a continuation of application Ser. No. 559,558 filed Mar. 18, 1975, now abandoned.

BACKGROUND AND SUMMARY OF THE INVENTION

The present invention relates to a method of chromatographic separation of fluid mixtures into fractions and to a chromatograph therefor and may be useful, for example, in the production of pure substances.

Known in the art is a method of continuous separation of fluid mixtures into three fractions by means of a moving adsorbent bed. Such method is described, for example, in U.S. Pat. No. 3,338,031. To a vertical chromatographic column with a descending adsorbent bed a side column is connected by its lower end to the point below the inlet of the fluid mixture being separated; in this side column the adsorbent linear velocity being controlled separately. Separated fractions are collected (as sorbing ability is increased) from the top section of the main column, top section of the side column and from the bottom section of the main column.

This prior art method, however, features an essential disadvantage residing in that, in addition to rather complicated process technology and operation, particle size of the sorbent and, hence, its separating ability are constantly changed due to the friction of the moving sorbent particles against the column walls and against each other.

Known in the art is another method of chromatographically separating a continuously fed fluid mixture of compounds into fractions using stationary columns with a fixed adsorbent bed by means of a chromatograph specially designed for this method. The chromatograph comprises 12 separating columns series-connected into a closed loop and adapted for simultaneously passing two independent gas streams through individual sections thereof. Separated fractions are discharged in the intersections between the columns, while the mixture being separated is continuously delivered into the middle section of one of the columns. The inlet points of the gaseous streams and the mixture of compounds to be separated and outlet points of the separated fractions are simultaneously switched over to the columns in the direction of the gaseous streams to a column length in equal time intervals. (Cf. P. E. Barker and R. E. Deeble, Analytical Chemistry, vol. 45, No. 7, June 1973, 1121).

Also known in the art is a method of chromatographic separation of a continuously fed fluid mixture of compounds into fractions using stationary columns with a fixed adsorbent bed by means of a special chromatograph. This chromatograph comprises stationary columns connected to a circulation circuit, an inlet means for the mixture to be separated, two gas paths and a detector, the columns being divided into three or more groups and connected to three groups of commutation means respectively connecting both gas inlets of the chromatograph with the inlets of said column groups, inlets and outlets of the columns with each other and with the inlet means of the mixture being separated, and with the outlet channels of the chromatograph in such a manner that in any position of the circuit two or more column groups are connected in series into one gas path; said inlet means for the mixture to be separated being connected to the middle section between said column groups, while the remaining column groups are included into another gas path. In equal time intervals, the inlet points of the gas streams and the mixture of substances to be separated and outlet points of the separated fractions are simultaneously switched over to respective columns in the direction of the gas streams to a length of one column group.

Both said last prior art methods and chromatographs therefor have a disadvantage residing in that the mixture is separated into two fractions only, while, to purify the desired product from both less-sorbing and more-sorbing impurities which is a typical problem in such purification, separation of the mixture into three fractions is required. To accomplish this object by said methods, the mixture to be separated should be passed twice through the system, whereby a specific output from a unit sorbent volume in the column is correspondingly decreased.

It is an object of the present invention to provide a method of chromatographic separation of fluid mixtures of compounds into fractions and a chromatograph therefor which ensure continuous separation of a mixture into three and more fractions by means of a circulation separation system using stationary columns.

This object is accomplished by that in the method of chromatographic separation of fluid mixtures of compounds into fractions in accordance with the present invention by means of circulating a continuously fed mixture to be separated within a system of several columns adapted for simultaneously passing two independent fluid streams through separate series-connected sections with synchronically replacing stream inlet and outlet points, the mixture is preliminarily separated, in accordance with the invention, by circulation within a system consisting of at least three separating columns, into two fractions discharged from the column system with separate fluid streams, one of the streams or both containing a preliminarily separated fraction in the form of a mixture of substances is respectively passed through one additional separating column or two such columns, wherein said fraction is separated into narrower fractions or individual components.

In a chromatograph intended for the realization of the method according to the present invention and comprising a system of stationary separating columns flushed with two separate fluid streams, a distributor of said streams between the inlets of the column system, a dosing device and a valve unit connecting outlets and inlets of the columns together, with the dosing device, with fluid outlets, in accordance with the present invention, in the body of the valve unit there are made three channels in the same direction, connected at one end thereof with the inlets of the columns and with the stream distributor outlets and at the other end connected with the outlets of the same columns. In a substantially transverse direction thereto in the same body there are provided three other channels plugged at one end thereof, while the other end of one of these channels is connected to the dosing device, two other ends being connected to the fluid outlets, and at each crossing of one channel over the other branch ducts from both channels are provided opening at the external surface of the body and covered in pairs with membranes thus forming nine membrane valves connecting said channels with each other, each of the channels connecting inlets and outlets of the columns with each other are interrupted under the membrane of the valve connecting said channel to the dosing device; one of the channels connecting the valve unit to the fluid outlets being provided with an additional separating column with a distributor of fractions at its outlet.

Such an arrangement of the chromatograph ensures direct separation of a mixture of compounds into three fractions.

It is abvisable that in the chromatograph for direct separation of a continuously fed fluid mixture into four fractions, in accordance with the present invention, in both channels connecting the valve unit to the fluid outlets separating columns be mounted provided with detecting means and fraction distributors.

BRIEF DESCRIPTION OF THE DRAWINGS

For a better understanding of the present invention a detailed description of the method of chromatographic separation of fluid mixtures into fractions and Examples illustrating the chromatograph embodiments are given with reference to the accompanying drawings, wherein:

FIGS. 1–6 show six successive operating positions of the chromatograph scheme for separation of a fluid mixture into three fractions in accordance with the method of the present invention;

DESCRIPTION OF THE PREFERRED EMBODIMENTS

Figure 7:
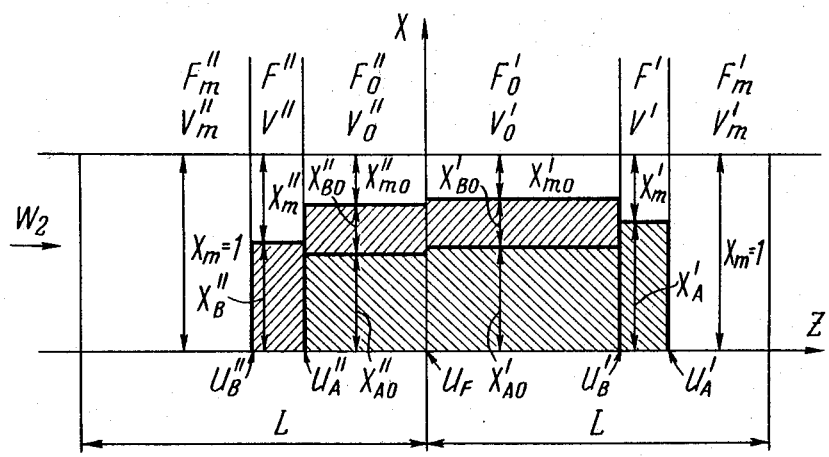
FIG. 7 is a diagram of a chromatographic band in the first two series-connected columns.

The principle of the present invention is schematically illustrated by FIGS. 1 through 6, wherein there are shown several working positions of the scheme of one of the possible embodiments of the chromatograph employed in the method of separating fluid mixtures of compounds into fractions.

The method according to the present invention is explained, in particular, for the case of a chromatographic separation of a ternary system with linear sorption isotherms and with independent distribution of the components between phases. The mixture contains, as an example, components A, B, and C, component A having the lowest sorption ability and component C — the highest, while component B has an intermediate sorption ability.

The chromatograph generally has separating columns 1, 2, and 3 connected to form a closed loop adapted for simultaneously passing two separate streams of the fluid and an additional column (or columns) 4 connected to the outlet of one or both streams. Columns 1, 2, and 3 are connected with each other by means of connecting ducts 5, wherein these are mounted controlled switching members 6, 7, and 8 embodied, for example, as controlled membrane valves. Each of the connecting ducts 5 has supplying lines 9 with mounted therein switching members 10 similar to members 6, 7, and 8. Supplying lines 9 are intended to introduce gas-vapour streams into the system of columns 1, 2, and 3, discharge gas from the system and deliver the binary fraction into the additional column 4. The number of supplying lines 9 provided in each connecting ducts 5 is defined by a total number of the streams fed into the system and discharged therefrom; in the particular case under consideration it is equal to 5 (introduced into the system are two streams of the carrier-gas and the stream of the mixture being separated A+B+C; discharged from the system is a stream of the fraction containing components A and B and a stream of the fraction enriched with component C, both streams being diluted with the carrier-gas). Series-connected to column 4 is a detector 11 providing signals for controlling a stopcock 12 for switching the stream leaving column 4 to channels 13 or 14 to distribute the fractions separated in column 4 and enriched respectively with component A or component B. Detector 11 is optional. Sampling of the fractions separated in column 4 may be controlled according to a certain time program. On the other hand, in some cases, to facilitate the system adjustment, it is advisable that a detecting means be connected to the inlet channel 15 of column 4, but due to the use of a frontal separation in columns 1, 2, and 3, said detecting means does not provide direct information in respect of the composition and purity of the fraction being detected.

In the chromatograph scheme position shown in FIG. 1 where valve 7 in the connecting duct 5 between columns 2 and 3 is opened and valves 6 and 8 are closed, column 1 is fed with a stream $W_1$ of a carrier-gas which is delivered from the outlet of the same column to a collector of fractions having greater sorbing ability and enriched with component C, while a stream $W_2$ of a carrier-gas is passed through columns 2 and 3 and then it is passed from the outlet of column 3 to column 4, wherefrom via channel 13 or 14 it is delivered into collectors for less-sorbing fractions enriched respectively with component A and component B (the collectors are not shown in FIGS. 1–6).

At the beginning of separation of fluid mixtures with established streams of carrier-gas $W_1$ and $W_2$, a stream of a vaporous (or gaseous) mixture containing three components A, B and C is fed into the column 3 through the inlet thereof. As the components of the mixture are passed across the adsorbent bed in column 3, the front of moving chromatographic band becomes enriched with the less-sorbing (more "light") component A due to the difference in distribution coefficients of the components. Since the velocities of the component movement along the adsorbent bed in column 3 are different for said components A, B and C, in column 3 three chromatographic bands are formed containing respectively component A, components A+B and components A+B+C. Starting from a particular moment when the forward front of the chromatographic band has reached the outlet of column 3, the fraction enriched substantially with component A enters column 4 along with the stream of carrier-gas $W_2$, followed by the fraction containing components A and B. Collection of the binary fraction A+B from the outlet of column 3 and supply of the mixture to be separated to the inlet of column 3 are effected up to that moment when a zone of the chromatographic band with equilibrium contents of components A, B and C approaches the outlet of column 3 (cross-hatched region A+B+C of column 3 in FIG. 1). At this moment the scheme is switched from the position shown in FIG. 1 to the position shown in FIG. 2, where valve 8 in the connecting duct 5 between columns 3 and 1 is opened, while valves 6 and 7 are closed. At the same moment replacement of inlet and outlet points of the carrier-gas and inlet point of the mixture being separated is effected by switching valves 10 mounted in the supplying lines 9. From this moment the stream of carrier-gas $W_1$ is delivered to the inlet of column 2 and discharged from the outlet of the same column into a collector for "heavy" fraction, while stream $W_2$ is delivered to the inlet of column 3 and discharged from the outlet of column 1 into column 4, and the mixture being separated is continuously fed to the inlet of column 1.

The zone of the chromatographic band containing component A in its head portion and components A and B in its rear portion and passed at the previous moment to column 4 is moved along column 4 under the action of stream $W_2$ while being separated into two zones, the first containing component A and the second (rear zone) — component B; both zones being diluted with the carrier-gas. The length of column 4 and stationary phase therein are selected so as to ensure the required degree of separation of the components A and B. It is also necessary to ensure that the zone of the light component A separated from a portion of binary fraction A+B which is fed into column 4 at the shown position of the scheme would not overtake the component B zone resulting from the previous supply of a portion of the binary fraction into column 4. Distribution of the fractions separated in column 4 and enriched respectively with component A and component B is controlled by means of stopcock 12 actuated by signals from detector 11.

The mixture separation process occuring in the scheme position shown in FIG. 2 in column 1 is fully identical to the above-discussed separation process in column 3 at the previous moment (FIG. 1). The portion of the mixture remaining in column 3 is passed, under the action of the stream of carrier-gas $W_2$, from column 3 into column 1. Due to different sorbing abilities of the components and, hence, different linear velocity of their movement, in column 3 three adjacent zones are formed containing respectively components A+B+C, B+C and C (in the direction opposite to the flow). When the forward front of the mixed zone A+B+C approaches the outlet of column 1 and the rear front of the zone containing components B and C leaves column 3, the gas circuit of the chromatograph is switched from the second position (FIG. 2) to the third position (FIG. 3). In this position of the scheme valve 6 between columns 1 and 2 is opened, while valves 7 and 8 are closed. Stream $W_1$ of the carrier-gas at this moment is switched over to the inlet of column 3, stream $W_2$ is switched over to the inlet of column 1, while the mixture being separated is continuously fed to the inlet of column 2. The remaining portion of the chromatographic band in column 3 enriched with the most sorbing component C is discharged with the stream of carrier-gas $W_1$ into the collector for heavy fractions of the mixture. The velocity of said stream of carrier-gas $W_1$ is selected so that before the moment of the next switching over of the valves the adsorbent in column 3 would be completely regenerated from the component C. The zone of the chromatographic band containing components A and B and remaining in column 4 is passed, under the action of the stream $W_2$, along column 4 while gradually separating into zones of pure components A and B which are discharged respectively via channels 13 and 14 into the collectors for corresponding fractions (not shown in the Figure). Starting from a particular moment when the head front of the chromatographic band reaches the outlet of column 2, a portion of the binary fraction A+B is again passed into column 4 along with the carrier-gas stream in the form of a zone of an appropriate length containing in its head portion predominantly component A and in its rear portion, components A and B. The bicomponent fraction A+B is delivered from the outlet of column 2 into column 4 untill the head front of the mixed zone A+B of the chromatographic band reaches the outlet of column 2 and the rear front of zone B+C completely leaves column 1, whereafter the chromatograph scheme is switched from the third position to the fourth one (FIG. 4). In this position of the scheme the stream of carrier-gas $W_1$ is delivered to the inlet of column 1 and discharged from the outlet of this column along with the portion of the chromatographic band remaining therein enriched with the heavy component C, into the collector for heavy fraction. The stream of carrier-gas $W_2$ is delivered to the inlet of column 2, while the mixture being separated is fed to the inlet of column 3 and collection of the binary fraction with subsequent supply thereof to the final separation in column 4 is effected from the outlet of column 3. Starting from this moment, separation cycles are repeated in the above-described succession. Separation of the continuously fed fluid mixture and collection of the fractions containing components A and B are effected by means of the carrier-gas stream $W_2$, while collection of the heavy fraction containing component C is effected by means of the carrier-gas stream $W_1$; the inlet and outlet points are replaced along series-mounted columns 1, 2 and 3 in synchronism with the switching over of the inlet point of the mixture being separated.

In doing so, during each cycle the stopcock 12 is switched at the same moments from one position to another and vice versa in the function of the arrival of the separated components A and B at the outlet of column 4. In the fifth position of the chromatograph scheme (FIG. 5) stopcock 12 is in the position ensuring discharge of the light fraction enriched with component A through channel 13. In FIG. 6 the chromatograph scheme is shown switched to the following sixth position but at the moment when stopcock 12 is switched to another position (comparing to FIGS. 1–5) and a portion of the fraction enriched with component B which has been fed into column 4 during the previous fifth cycle (FIG. 5) is discharged via channel 14.

Another embodiment of the method according to the present invention is possible. Column 4 may be also fed with the carrier-gas stream $W_1$ instead of $W_2$. In this case the separation process is similar to that described hereinabove with the only difference that the scheme is switched to the next position at the moment when the forward front of the mixed zone A+B reaches the outlet of the column fed with the mixture and the rear front of the mixed zone A+B+C has already left the other column flushed with the same carrier-gas stream $W_1$. The remaining portion of the chromatographic band containing in its head portion components B and C and, in its rear portion, the most sorbing component C, is discharged with the carrier-gas stream $W_1$ into column 4, wherein it is separated in a manner similar to that described hereinabove, into the fractions respectively enriched with component B and component C which are discharged from the column system via channels 13 and 14.

The choice of a particular embodiment depends on specific conditions such as, for example, difference in the component sorbing abilities and sharpness of the fronts separating individual zones of the chromatographic band.

Positions of zones of the components being separated and their concentrations in the two-section branch of the chromatograph circuit are schematically shown in FIG. 7, wherein F denotes a volume velocity, V — linear velocity of the total stream in this zone, U is a linear velocity of a respective front; $X_a$, $X_b$ and $X_m$ are molar parts of components A and B and carrier-gas respectively. The superscript (') denotes the first section in the direction of stream $W_2$ (for example, column 1 in the scheme position shown in FIG. 2), while superscript ('') denotes the second section (column 3 in the scheme position shown in FIG. 2). Section length is denoted by L. For the sake of better understanding, a binary mixture is discussed. At the initial moment the whole chromatographic band is in the second section (left-hand side in FIG. 7), wherefrom it becomes moving into the right-hand section under the action of the carrier gas stream $W_2$. In the point $Z = 0$ (intersection between columns) a fresh stream of the mixture being separated is added at a volume velocity $F_F$, whereby the concentration of components A and B in the carrier-gas is increased. At the equal flow rate through both columns, i.e. when $F_F = 0$, the rear front velocity $U_A''$ of the less-sorbing component A is higher than the forward front velocity $U_B'$ of the more sorbing component B. At $F_F > 0$, the flow rate in the first column is higher than the flow rate in the second column and front velocities in the latter are decreased the more the higher is the difference between the flow rates in both columns. Ultimate condition for the maximum supply rate of the mixture being separated is: $U_A'' = U_B'$, i.e. by the moment when the zone of component B approaches the outlet of the first column, the zone of component A leaves the second column. When the mixture supply rate is above this limit, simultaneous separation of both components in the pure form is impossible.

Regarding, for the sake of better understanding, practically non-sharp fronts as being sharp, it is possible to show, with certain assumptions, that $$F_{F\ max} = F_m'' (\alpha - 1) \qquad (1)$$

where separation factor of two compounds A and B is:

$$\alpha = \frac{q_B}{q_A}$$

and $q_A$ and $q_B$ are factors of the components distribution between phases.

Consequently, the maximum permissible supply rate of the mixture being separated depends linearly on the carrier-gas velocity and, at a certain velocity of the carrier-gas it is the higher the more selective the employed adsorbent is.

Cycle duration T between successive switchings under the same conditions is expressed as:

$$T = \frac{V_A}{F_{F\ max}} (\alpha - 1) \qquad (2)$$

where $V_A$ is a retention volume of component A.

General condition for separation of a multi-component mixture into two fractions with components numbered i and i+1 according to the increase in sorbing abilities thereof is:

$$U''_i \geq \frac{L}{T} \geq U'_{i+1} \qquad (3)$$

Figure 8:
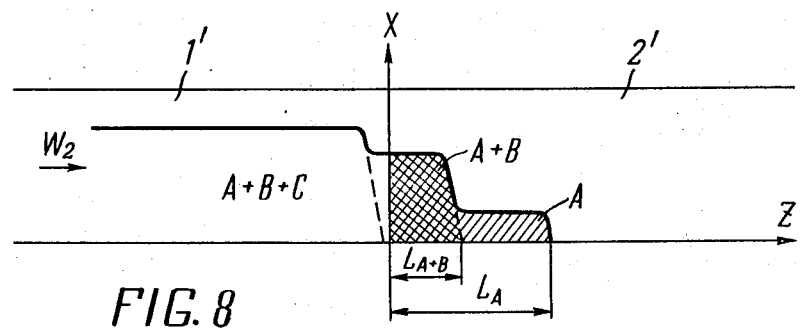
FIG. 8 is a schematic diagram of a portion of the mixture fed into the additional column for the purpose of its final separation in accordance with one embodiment of the method of the present invention.

The zone of the chromatographic band, fed in accordance with the description into column 4, containing component A in its head portion and components A and B in its rear portion is schematically shown in FIG. 8 at the moment of column switching-over; $I'$ denotes column 3 in the position shown in FIG. 1, column 1 — in the position shown in FIG. 2, etc., while column 4 is denoted by numeral 2. The fraction being separated is introduced into column 4 in the form of a relatively long plug where the components being separated are already pre-oriented.

Moving, under the action of the carrier-gas stream $W_2$, along said column 4, the plug of the introduced fraction is separated into two zones, the first (in the direction of the stream) containing component A, the second (rear zone) containing component B. Since the more sorbing component B at the entrance to column 4 is already in the rear, for the determination of the parameters of column 4 importance lies with the length $l_{A+B}$ of the mixed zone A+B, and not with the total plug length $L_A$. Taking into consideration the fact that the length of column 4, stationary phase of this column and separation temperature may be chosen irrespective of the parameters of columns 1, 2 and 3, it is evident that it is possible to ensure purification of the desired component B from light impurities simultaneously with circulating fractionation. It should also be noted that there is no necessity to synchronize the time of passing the mixture plug through column 4 with the cycle duration T between successive switchings of the chromatograph scheme.

Figure 9:
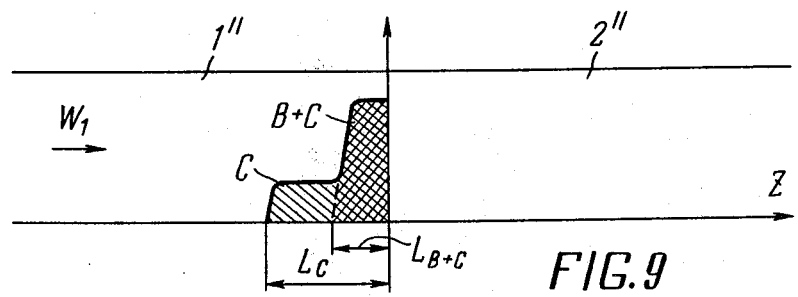
FIG. 9 is a similar diagram in accordance with another embodiment of the method of the present invention.

The scheme position corresponding to another embodiment of the process, discussed hereinabove, when column 4 is fed with the carrier-gas stream $W_1$, is shown in FIG. 9, wherein 2'' denotes column 4, 1'' denotes column 1 in the position shown in FIG. 1, column 2 in the position shown in FIG. 2, column 3 in the position shown in FIG. 3, etc. After another switching of the scheme, the cut-off portion of the chromatographic band is at the outlet of the regeneration section of the chromatographic loop (for example, column 1 in the position shown in FIG. 4) and discharged therefrom into column 4 by means of the carrier-gas stream $W_1$. In this case, the less-sorbing desired component B in a mixture with component C is in the head portion of the plug, while in the rear portion thereof is a pure zone of the more sorbing impurity C.

Generally, in the purification of the desired component from impurities, the desired component is component B, while components A and C represent total light and heavy impurities respectively.

In columns 1, 2 and 3 a substantially equal temperature is maintained. However, to increase efficiency of separation of fluid mixtures, an excessive lagging of the rear fronts in the chromatographic band when the mixture supply rate exceeds the above-mentioned limit may be compensated by elevating the temperature of that column from among the columns 1, 2 and 3 which in this position is fed with the carrier-gas stream $W_2$, wherefor each of columns 1, 2 and 3 may be provided with individual temperature control means.

In the separation of vapours and gaseous mixtures based on the displacement principle, as $W_2$ stream use is made, instead of a carrier-gas, of a displacing gas employed either individually or diluted with an inert carrier-gas. In this case the process, in general, is similar to that described hereinbefore with the only difference that the chromatographic band movement and separation of the mixture in the first column of the two-stage section of the chromatographic loop (column 2 in FIG. 4, etc.) are effected under the action of an expanding zone of the displacing agent being sorbed which displaces the mixture components from the column. As the displacing medium it is advisable to employ, for example, a portion of the separated heavy fraction stream. Velocity of the carrier-gas in the stream $W_1$ is selected so that the column flushed with $W_1$ stream could be completely regenerated from the displacing gas during one cycle.

In the mixture separation by methods of liquid chromatography, streams $W_1$ and $W_2$ are formed by liquids disssolving the components of the mixture being separated. These two streams $W_1$ and $W_2$ provide better conditions for the use of gradient elution in order to improve separation conditions and to enhance the system efficiency.

Depending on particular separation conditions and properties of the mixture components, each of the three columns 1, 2 and 3 may be formed of one or more series-connected sections of equal length with replacing each time inlet and outlet points to a length of one section. Therefore, functional parts of the scheme may have different lengths.

Figure 10:
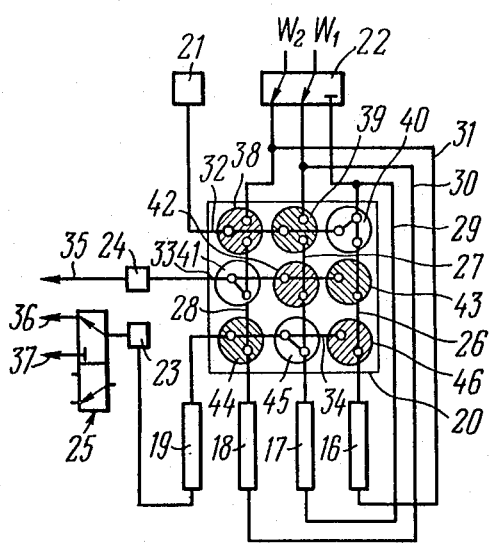
FIGS. 10–12 show successive operating positions of the chromatograph gas system in accordance with an embodiment of the method of the present invention for separation of the fluid mixture into three fractions.
Figure 11:
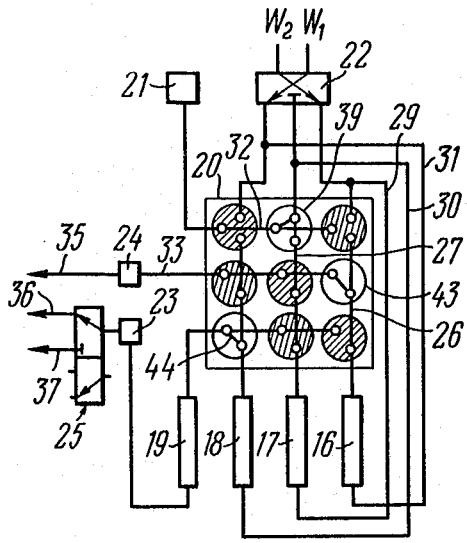
Figure 12:
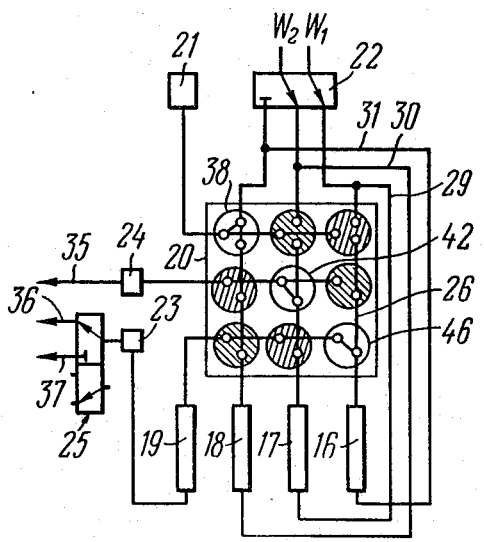

The above-described method of chromatographically separating fluid mixtures of compounds into fractions may be preferably performed using a chromatograph shown in FIGS. 10, 11 and 12. The chromatograph comprises four stationary separating columns 16, 17, 18 and 19 (respectively columns 1, 2, 3 and 4 in FIGS. 1–6), valve unit 20 (respectively switching elements 6, 7, 8 and 10 in FIGS. 1–6), dosing device 21, a distributor 22 of the fluid mixture streams among the inlets of columns 16, 17, 18, detectors 23 and 24 and fraction distributor 25 (corresponds to stopcock 12 in FIGS. 1–6). In the body of valve unit 20 three channels are made in the same direction, i.e. channels 26, 27 and 28 connected at one end thereof to the outlets of columns 16, 17 and 18 and, at the other ends, to the inlets 29, 30 and 31 of the same columns and to the outlets of the stream distributor 22. In a substantially transverse direction to channels 26, 27 and 28 in the body of valve unit 20 there are channels 32, 33 and 34 which are plugged at one end each. The other end of channel 32 is connected to the dosing device 21, while other ends of channels 33 and 34 are connected to the outlets 35, 36 and 37 of the chromatograph (outlets 36, 37 correspond to channels 13, 14 in FIGS. 1–6). Channels 26, 27, 28 and 32, 33 and 34 be in different planes and do not intersect. At each passage of one channel over another, branch ducts are provided opening at the external surface of the body of valve unit 20 and covered, in pairs, by common membranes thus forming nine membrane valves 38, 39, 40, 41, 42, 43, 44, 45 and 46. Each of the channels connecting inlets and outlets of columns 16, 17 and 18 together is interrupted under the membrane of the valve connecting said channel to the dosing device 21. Valves 38–46 are closed when pressure acts on membranes and opened when the pressure is released above the membranes under the action of pressure in the controlled path. Valves 38, 42, 46, valves 39, 43, 44 and valves 40, 41, 45 operate in synchronism. Between channel 34 and outlets 36 and 37 of the chromatograph a column 19 is mounted in the path with a detector 23 and fraction distributor 25 provided at the outlet of said column. A detector 24 is also mounted in the path before outlet 35.

Type and connection scheme of detectors 23 and 24 depend on particular conditions and do not constitute subject matter of the present invention. In general, a flame-ionization detector may be used. These detecting means are, however, optional. The separation process and collection of fractions may be also time-controlled.

Arrangement of the stream distributor 22 and fraction distributor 25 is out of the scope of the present invention. Any conventional arrangement may be used, provided it meets corresponding requirements.

Figure 13:
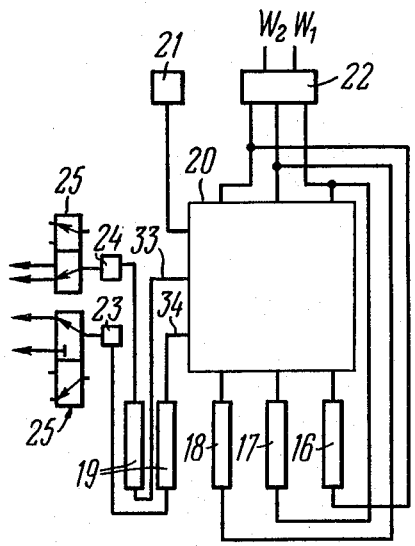
FIG. 13 is a schematic diagram of the chromatograph embodiment for separation of the fluid mixture into four fractions.

Column 19 with detector 23 and fraction distributor 25 may be mounted at the outlet of channel 33. In the separation of the mixture into four fractions, additional columns 19 with fraction distributors 25 are located at the outlets of both channels 33 and 34 (FIG. 13).

The chromatograph functions in the following manner. In the position shown in FIG. 10, valves 40, 41 and 45 are opened, while the remaining valves are closed. A stream of the fluid mixture, for example carrier-gas $W_1$, fed into the chromatograph through the steam distributor 22 is passed into column 16 through the inlet 31 and from the outlet of column 16 it is further passed via channel 26 into a membrane valve 40, whereinto the carrier-gas stream $W_2$, a stream of the mixture containing, for example, components A, B and C, from the dosing device 21 via channel 32 at a constant volume speed is added. Then, the common stream of the carrier-gas with the mixture being separated is passed through the inlet 29 into the column 17 and further through the membrane valve 45 into column 19. From column 19 said stream is passed through detector 23 and fraction distributor 25 to the chromatograph outlets 36 and 37. Another stream $W_1$ at the same time is passed through the stream distributor 22 to the inlet 30 into the column 18, wherefrom it is further passed through channel 28, membrane valve 41 and detector 24 to the chromatograph outlet 35.

As the components are moved across the adsorbent bed in column 17, the front of the moving chromatographic band become enriched with the less-sorbing component A due to the difference in the distribution coefficients of the components. Since the velocities of components A, B and C in the column are different, three successive chromatographic zones are formed in column 17 containing respectively component A, components A+B and components A+B+C. Starting from a particular moment when the forward front of the chromatographic band reaches the outlet of the column 17, along with the carrier-gas stream a fraction enriched mainly with component A is first passed into column 19, followed by the fraction containing components A and B. Collection of the two-component fraction from the outlet of column 17 is effected till the zone of the chromatographic band with equilibrium contents of components A, B and C approaches the outlet of column 17. At this moment the chromatograph scheme is switched over to another position (FIG. 11). Valves 39, 43 and 44 are opened, valves 40, 41 and 45 are closed, and valves 38, 42 and 46 remain still closed. In this position of the scheme, stream $W_1$ is passed through inlet 31, column 16, channel 26, valve 43, channel 33 and detector 24 to the chromatograph outlet 35.

Stream $W_2$ in this scheme position is passed through inlet 29 into column 17, further via channel 27 into the membrane valve 39, where it is added with the stream of the mixture being separated fed through channel 32. The combined stream is further passed through inlet 30 into column 18, wherefrom through valve 44 it goes into column 19 and further through detector 23 and fraction distributor 25 to the chromatograph outlets 36 and 37.

The chromatographic band zone, being present in column 19 and containing in its head portion the less-sorbing component and a mixture of components A and B in its rear portion is separated, as it moves along column 19, into zones containing, respectively, components A and B. In accordance with the signals of detector 23, fraction distributor 25 distributes said components A and B between outlets 36 and 37.

The separation process occuring in column 18 in this position of the chromatograph scheme is identical with the process described for the case of column 17 in the previous position. At the same time the zone of the chromatographic band remaining in column 17 and having equilibrium contents of components A, B and C, starts moving, under the action of the carrier-gas stream, from column 17 into column 18. Due to different velocities of the components movement, in the rear portion of the chromatographic band a zone of the most sorbing component C is formed, preceded by the zone of components B+C.

Collection of the binary fraction from the outlet of column 18 in the position shown in FIG. 11 and supply of the mixture being separated to the inlet of column 18 are effected till the moment when the zone of the chromatographic band with equilibrium content of components A, B and C arrives at the outlet of column 18 and the zone B+C has already left the column 17. At this moment the chromatograph is switched over to the next position (FIG. 12). In this position valves 38, 42 and 46 are opened, while the remaining valves are closed. The regeneration stream $W_1$ is passed through the stream distributor 22, inlet 29, column 17, valve 42 to outlet 35 entraining therewith the zone left at the outlet of column 17, enriched with the best-sorbing component C. Flow rate of stream $W_1$ is selected so that column 17 would be completely regenerated from the component C during the cycle. Stream $W_2$ is passed through the series-connected columns 18, 16 and 19. The mixture is fed to the inlet 31 of column 16, while the binary fraction is discharged into column 19 from the outlet of column 16 via channel 26 and valve 46. The separation process occuring in columns 18 and 16 is identical with the process occuring at the preceding moment in columns 17 and 18. Separation process in column 19 is the same in all the positions.

At the moment when the zone of the chromatographic band having equilibrium content of components A, B and C arrives at the outlet of column 16, and the zone containing components B+C has already left the column 18, the scheme is switched from its last position (FIG. 12) over to the initial position (FIG. 10) and the process is continued in the above-described sequence.

In the separation of a four-component mixture, the outlet of channel 33 is connected to another column 19 with another fraction distributor 25. The separation process in this case is similar to the above-described with the only difference that the mixture is preliminarily separated, by way of circulation in the system of columns 16, 17 and 18, into binary fractions which are further finally separated in additional columns 19.

To separate a particular component from a multi-component mixture, the separation conditions are selected so that the less- or better-sorbing impurities (with column 19 positioned at the outlet of channel 33 or 34) would be separated by means of circulation in columns 16, 17 and 18, while better- or less-sorbing impurities would be separated, respectively, in column 19.

In a particular case, in the separation of a binary mixture said column 19 with the fraction distributor may be dispensed with, since leaving channels 33 and 34 are already separated fractions enriched with the less- and better-sorbing components respectively.

To facilitate the chromatograph adjustment, a detector may be also provided in the path at the outlet of channel 34 before column 19.

In the experimental tests of the method according to the present invention in purification of n-hexane from inpurities, a 500 ml/hr load was obtained at columns of 24 mm in diameter with the desired product purity of 99.99%. Increase in the output as compared to conventional batch process under comparable conditions with the maximal densification of the chromatogram is, according to the experimental test results, up to 30 times. Increase in the specific load per unit of the packing volume is, on an average, up to 7 times due to the difference in total length of the columns in both cases.

Therefore, in accordance with the above-discussed theoretical considerations, the output increase is explained by more efficient use of the adsorbent in the column due to continuous supply of the mixture to be separated, but not by the separation improvement.

What is claimed is:
1. A method of chromatographic separation of fluid mixtures into fractions using four chromatographic columns connected into a circulation path adapted for simultaneous passing of two independent carrier gas streams through separated series parts of said path, in which method at each moment one column acts as enriching column, the second as stripping column, the third as regenerating column, the fourth acting as eluting column, the method comprising steps of:
   a. continuously introducing the mixture to be separated at constant flow rate into a pipe connecting the stripping column to the enriching column;
   b. recovering at the outlet of the enriching column a preselected fraction of the mixture containing at least one preselected component of the mixture mixed with other less strongly adsorbed components of the mixture;
   c. feeding said preselected fraction of the mixture into the eluting column;
   d. rearranging the columns so that the previously regenerating column now acts as the enriching column, the previously enriching column acting as stripping column and the previously stripping column now acting as regenerating column;

e. recovering a fraction of the mixture enriched in more strongly adsorbed components of the mixture at the outlet of the renererating column; and f. separating said preselected fraction in said eluting column into at least two fractions from which one fraction is enriched in said preselected component with recovery of said fractions at the outlet of the eluting column; the separation and recovering of the fractions enriched in less strongly adsorbed components of the mixture and in said preselected component being carried out by means of the first carrier gas stream, the recovering of the fraction enriched in more strongly adsorbed components being carried out by means of the second carrier gas stream.

2. A method of chromatographic separation of fluid mixtures into fractions using four chromatograhic columns connected into a circulation path adapted for simultaneous passing of two independent carrier gas streams through separated series parts of said path, in which method at each moment one column acts as stripping column, the second as enriching column, the third as regenerating column, the fourth acting as eluting column, the method comprising steps of:

a. continuously introducing the mixture to be separated at constant flow rate into a pipe connecting the enriching column to the stripping column;

b. recovering a fraction of the mixture enriched in less strongly adsorbed components of the mixture at the outlet of the stripping column;

c. rearranging the columns so that the previously stripping column now acts as enriching column, the previously enriching column now acting as regenerating column and the previously regenerating column now acting as stripping column;

d. recovering at the outlet of the enriching column a preselected fraction of the mixture containing at least one preselected component of the mixture mixed with other more strongly adsorbed components;

e. feeding said preselected fraction of the mixture into the eluting column; and f. separating said preselected fraction in said eluting columns into at least two fractions from which one fraction is enriched in said preselected component with recovery of said fractions at the outlet of the eluting column; the separation and recovery of the fraction enriched in less strongly adsorbed components of the mixture being carried out by means of the first carrier gas stream, the separation and recovering of the fractions enriched in said preselected component and in more strongly adsorbed components of the mixture being carried out by means of the second carrier gas stream.

3. Apparatus for chromatographic separation which comprises:

a. first, second, third and fourth chromatographic separating columns;

b. first and second sources of carrier gas;

c. means for passing said first carrier gas stream through said first, second and fourth separating columns connected in series;

d. means for continuously introducing a mixture to be separated at constant flow rate into a pipe connecting said first and second columns;

e. means for passing said second carrier gas stream through said third column simultaneously with the passing of said first carrier gas stream through the other columns;

f. means for removing a fraction of the mixture enriched in more strongly adsorbed components from the outlet of said third separating column;

g. means for removing at least two fractions of the mixture enriched correspondingly in a preselected component of the mixture and in less strongly adsorbed components from the outlet of said fourth separating column; and h. means for shifting the inlet points of the mixture to be separated, the inlet of the fourth column and the inlet and outlet points of said carrier gas streams along said first, second and third column in the direction of gas flow periodically and simultaneously, each time said third column being connected between said second and fourth columns, said second column being isolated.

4. Apparatus for chromatographic separation which comprises:

a. first, second, third and fourth chromatographic separating columns;

b. first and second sources of carrier gas;

c. means for passing said first carrier gas stream through said first and second separating columns connected in series, d. means for continuously introducing a mixture to be separated at constant flow rate into a pipe connecting said first and second columns;

e. means for passing said second carrier gas stream through said third and fourth separating columns connected in series, simultaneously with the passing of said first carrier gas stream through the other columns;

f. means for removing a fraction of the mixture enriched in less strongly adsorbed components of the mixture from the outlet of said second separating column;

g. means for removing at least two fractions of the mixture enriched correspondingly in a preselected component of the mixture and in more strongly adsorbed components from the outlet of said fourth separating column; and h. means for shifting the inlet points of the mixture to be separated, the inlet of the fourth column and the inlet and outlet points of said carrier gas streams along said first, second and third columns in the direction of gas flow periodically and simultaneously, each time said third column being connected to the outlet of said second column and said fourth column to the outlet of said first column.

5. The apparatus according to claim 4, wherein said means for shifting the inlet points of the mixture to be separated, the inlet of the fourth column and the inlet and outlet points of said carrier gas streams are made in the form of a valve unit having a body with three channels made in it in one direction and connected at one end to the first, second and third column inlets and with the means for passing said carrier gas streams through the columns, and at the other end connected to the outlets of the same columns, while in a substantially transverse direction to said channels in the same body three other channels are made being plugged at one end thereof, the other end of one of said three latter channels being connected to the means for continuously introducing the mixture to be separated, at each crossing of one channel over the other a membrane valve being mounted connecting said channels with each other, each of the channels connecting the inlets and outlets of the columns together being interrupted under the membrane of the valve connecting said channel to the means for introducing the mixture, while the inlet of the fourth column is connected to the free end of one of said two channels being plugged at the other end thereof.

* * * * *